US012617903B2

(12) United States Patent　　(10) Patent No.: US 12,617,903 B2
Kessler et al.　　(45) Date of Patent: May 5, 2026

(54) PROCESS FOR PRODUCING A COMPOSITION COMPRISING A CROSSLINKED HYDROGEL

(71) Applicant: MERZ PHARMA GMBH & CO. KGAA, Frankfurt am Main (DE)

(72) Inventors: Wolfgang Kessler, Berlin (DE); Roland Stragies, Berlin (DE); Alexander Linko, Frankfurt am Main (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 897 days.

(21) Appl. No.: 17/779,252

(22) PCT Filed: Dec. 8, 2020

(86) PCT No.: PCT/EP2020/085005

§ 371 (c)(1),
(2) Date: May 24, 2022

(87) PCT Pub. No.: WO2021/116069

PCT Pub. Date: Jun. 17, 2021

(65) Prior Publication Data

US 2023/0002564 A1　　Jan. 5, 2023

(30) Foreign Application Priority Data

Dec. 9, 2019　(EP) ..................................... 19214541

(51) Int. Cl.
| | |
|---|---|
| *C08J 3/075* | (2006.01) |
| *A61K 8/73* | (2006.01) |
| *A61L 27/20* | (2006.01) |
| *A61L 27/52* | (2006.01) |
| *A61Q 19/08* | (2006.01) |
| *C08B 37/08* | (2006.01) |
| *C08J 3/24* | (2006.01) |

(52) U.S. Cl.
CPC .............. *C08J 3/075* (2013.01); *A61K 8/735* (2013.01); *A61L 27/20* (2013.01); *A61L 27/52* (2013.01); *A61Q 19/08* (2013.01); *C08B 37/0072* (2013.01); *C08J 3/247* (2013.01); *A61L 2400/06* (2013.01); *A61L 2430/34* (2013.01); *C08J 2305/08* (2013.01)

(58) Field of Classification Search
CPC ........ C08J 3/075; C08J 3/247; C08J 2305/08;

A61K 8/735; A61L 27/20; A61L 27/52; A61L 2400/06; A61L 2430/34; A61Q 19/08; C08B 37/0072
USPC ........................................................ 536/55.1
See application file for complete search history.

(56) References Cited

U.S. PATENT DOCUMENTS

| | | | |
|---|---|---|---|
| 6,561,266 B1 | 5/2003 | Ehrlicher | |
| 8,052,990 B2 | 11/2011 | Hermitte et al. | |
| 2005/0281880 A1 | 12/2005 | Wang | |
| 2018/0282440 A1* | 10/2018 | Babar | ....................... C08F 2/22 |

FOREIGN PATENT DOCUMENTS

| | | |
|---|---|---|
| CN | 202849302 U | 4/2013 |
| DE | 19848780 C1 | 5/2000 |
| DE | 10202084 A1 | 8/2003 |
| WO | 2013185934 A1 | 12/2013 |
| WO | 2017036597 A1 | 3/2017 |

OTHER PUBLICATIONS

International Preliminary Report on Patentability in International Application No. PCT/EP2020/085005, dated May 17, 2022.

\* cited by examiner

*Primary Examiner* — Yih-Horng Shiao

(74) *Attorney, Agent, or Firm* — RAPHAEL BELLUM PLLC

(57)　　ABSTRACT

A process for producing a composition comprising a crosslinked hydrogel is proposed. The process comprises providing a container body (2), wherein the container body (2) has a body inner wall (21) and a body outer wall (22), wherein the body inner (21) wall is configured to be tempered, filling of a fluid (7) comprising at least a mixture of a polymer and water into the container body (2), and agitating the fluid. For crosslinking of the fluid (7), a container insert (3) is provided, the container insert (3) having an insert outer wall (32) which is configured to be tempered and a container assembly (1) is formed by inserting the container insert (3) into the container body (2) so that the insert outer wall (32) of the container insert (3) and the body inner wall (21) of the container body (2) are separated by a gap (9) of constant width and define a volume (6) for receiving the fluid (7). Crosslinking of the fluid (7) is then performed while tempering the insert outer wall (32) and the body inner wall (21) to form a crosslinked hydrogel.

20 Claims, 3 Drawing Sheets

PROCESS FOR PRODUCING A COMPOSITION COMPRISING A CROSSLINKED HYDROGEL

The invention relates to a process for producing a composition comprising a crosslinked hydrogel, wherein a container is provided, the container is filled with a fluid, the fluid is agitated and then crosslinked. Further aspects relate to a composition obtained by this process and the use of the obtained composition.

STATE OF THE ART

It is known in the art to use gels such as hydrogels based on polysaccharides and water as dermatological fillers. Hydrogels are networks of polymer chains that are hydrophilic. The hydrophilic polymer chains are held together by crosslinks. Such gels are generally prepared by methods comprising the chemical crosslinking of the respective polysaccharides in an aqueous medium. Suitable polysaccharides are e.g. based on hyaluronic.

Hyaluronic acid is a polymer natural to the body, which since some time is employed in medicine in different fields such as in orthopedics and in ophthalmology. Nowadays, hyaluronic acid is increasingly used in aesthetic medicine and in plastic surgery. The broad application of hyaluronic acid is particularly due to its very high binding capability of water. In aqueous medium, even at low concentration of hyaluronic acid, viscoelastic gels are formed, which are biologically degradable, and which have advantageous properties.

In the production of hyaluronic acid hydrogels, the precursors are first mixed in a mixing vessel and are then usually bottled in glass bottles for crosslinking of the hydrogel. For the process of crosslinking, the bottles are placed into a climate chamber so that the process may be carried out at constant temperature.

Processes for preparing hydrogels, in particular hydrogels based on hyaluronic acid, are known in the art. WO2013/185934 A1 discloses a method of preparing a composition comprising a crosslinked first polymer and optionally a second polymer, which may be crosslinked-or non-crosslinked. The polymers are selected from a polysaccharide and the method comprises crosslinking of a mixture comprising at least the first polymer and water, terminating the crosslinking, optionally blending with the second polymer and subjecting the obtained product to dialysis.

U.S. Pat. No. 8,052,990 B2 discloses a process for the production of a biocompatible crosslinked polydensified monophasic gel, comprising a crosslinking reaction of a predetermined quantity of at least one biocompatible polymer in solution by the addition of a quantity of crosslinking agent in a first volume of a reaction mixture and adding a supplemental quantity of polymer of a molecular weight higher than 500 000 Da in solution with dilution of the reaction mixture so as to decrease an overall concentration of the polymer in a second volume of the reaction mixture, continuing the crosslinking in the second volume and stopping the crosslinking reaction a drastic reduction of pH and temperature.

In order to increase throughput in the production of the hydrogels, it would be advantageous to carry out the step of crosslinking within the mixing vessel. For temperature control, the mixing vessel may be used to heat the contained product during crosslinking.

Vessels for mixing and tempering of products are known in the art. Such vessels comprise an agitator for mixing of the contained product and further comprise means for heating or cooling of the product.

A machine for mixing and homogenizing of products is known from DE 102 02 084 A1. The machine has a mixing vessel which is heated or cooled by means of a double wall. A homogenizer is arranged at the lowest point of the vessel together with an additional chopper which also mixes the contents of the vessel.

DE 198 48 780 C1 discloses a homogenization and tempering container for homogenizing and tempering of a liquid. The container comprises a heat exchanger arranged at a distance from the container walls which is surrounded by at least one partition wall dividing the container into concentric annular chambers. A recirculation pump is used for recirculating a partial volume of the liquid charge of the container from an outlet of the container to an inlet of the container. The concentric annular chambers are divided in in such a way that a flow path of the recirculated partial liquid runs in countercurrent direction through the heat exchanger and the annular chambers. The circulated liquid is both tempered and homogenized.

However, when the crosslinking of a hydrogel is performed within a mixing vessel, it has been observed that undesired solid particles form during the step of crosslinking, especially during the crosslinking of hyaluronic acid. This problem becomes worse when the size of the mixing vessel is increased, making it difficult to scale up the crosslinking process from a laboratory to a production scale.

It is an object of the present invention to provide a process which may be carried out in a container assembly for mixing and tempering of a fluid which overcomes the limitations of the known processes for the production of crosslinked hydrogels and in particular allows for crosslinking of hydrogels at a large scale.

DISCLOSURE OF THE INVENTION

A process for producing a composition comprising a crosslinked hydrogel is proposed. The process comprises providing a container body, wherein the container body has a body inner wall and a body outer wall, wherein the body inner wall is configured to be tempered, filling of a fluid comprising at least a mixture of a polymer and water into the container body, and agitating the fluid. For crosslinking of the fluid, a container insert is provided, the container insert having an insert outer wall which is configured to be tempered and a container assembly is formed by inserting the container insert into the container body so that the insert outer wall of the container insert and the body inner wall of the container body are separated by a gap of constant width and define a volume for receiving the fluid. Crosslinking of the fluid is then performed while tempering the insert outer wall and the body inner wall to form a crosslinked hydrogel.

The product obtained by the proposed process is a hydrogel. The term "gel" as used herein encompasses a product, which has both viscous and elastic properties. Thus, the term encompasses a viscoelastic product. In popular science, a gel sometimes is characterized as a jelly-like material. The viscoelastic properties of a gel may be determined by determining the loss modulus and the storage modulus of the gel. The ratio between the loss module G'' and the storage module G' may be expressed by the loss factor $\tan \delta = G''/G'$. The viscosity of the product may be expressed in terms of $\eta^*$ (complex viscosity). Suitable methods for determining $\tan \delta$ and $\eta^*$ are known in the art.

The used polymer is preferably a hyaluronic acid and/or a sodium salt thereof. Hyaluronic acid is a non-crosslinked polymer of disaccharides. It can have up to 25,000 disaccharide units in length. The molecular weight of hyaluronic acid may range from 5,000 to 20,000,000 Da.

The term "crosslinking" as used herein encompasses the linking of at least two different polymer chains of the polymer, in particular of hyaluronic acid, by means of a chemical bond or chemical bonds. As a consequence, molecular weight of the polymer is increased, and thus viscosity and/or elasticity of the hydrogel.

Preferably, crosslinking is performed via a crosslinker which is included in the fluid or added to the fluid prior to the step of crosslinking. Suitable crosslinkers for crosslinking polymers such as hyaluronic acids are known in the art.

Preferably, a crosslinker based on an epoxide-structure is used.

Preferably, a diglycidyether is used for the crosslinking.

A suitable diglycidyether is 1,4-butanediol diglycidylether (BDDE). This compound is commercially available.

Preferably, the crosslinker is used in a quantity of from 5 to 15% (volume crosslinker/weight of the polymer), such as 6 to 14% (v/w), or 7 to 12% (v/w).

The water of the mixture may be provided in the form of pipe water, distilled water, deionised water or water for pharmaceutical use, such as purified water, highly purified water or WFI (water for injection).

Preferably, the mixture additionally comprises a buffer solution, such as, for example a phosphate buffer solution.

Preferably, such a phosphate buffer solution is made from sodium chloride, dibasic anhydrous sodium phosphate, monobasic sodium phosphate dihydrate and water.

Alternatively, the buffer is an alkaline buffer.

Preferably, the pH of the buffer is from 6.8 to 7.6, or from 7.0 to 7.4, or from 7.1 to 7.3.

Preferably, the pH of the final composition prepared according to the described process is adjusted to a range of from 6.5 to 7.5 such as 6.7 to 7.2, or 6.8 to 7.1 or 6.8 to 6.9. Such pH may support the compatibility of the composition with skin tissue. For the adjustment of said pH it is preferred to use one of the described buffers.

Preferably, the cross-linking is performed at alkaline conditions. The temperature in the crosslinking reaction is controlled by means of tempering of the body outer wall and the insert inner wall.

During the crosslinking, the fluid may not be agitated. Any heat transport within the fluid occurs by heat conduction as the hydrogel does not allow convection. Thus, any addition or removal of heat must occur through the surfaces of the fluid and is limited by heat conduction within the fluid. The further away a certain part of the volume of the fluid is form a tempered surface, the more time is required to reach a predetermined temperature set point and the more time is required to achieve a stable and homogeneous temperature distribution within the entire volume of the fluid.

In usual mixing containers with a tempered wall, the average distance of the liquid to a tempered wall increases when the size of the container is increased. Accordingly, with increasing size of the container the homogeneity of the temperature distribution is reduced. If crosslinking is performed with such a mixing vessel and thus for a fluid having a non-homogenous temperature distribution, it has been observed that the crosslinking reaction is not proceeding uniformly and undesired solid particles form during the step of crosslinking, especially during the crosslinking of hyaluronic acid. This problem becomes worse when the size of the mixing vessel is increased, making it difficult to scale up the crosslinking process from a laboratory to a production scale.

The proposed process makes use of a container assembly comprising a container body having a tempered body inner wall and a container insert having a tempered insert outer wall. The body inner wall and the insert outer wall form a gap of uniform width which defines a volume for receiving the fluid during the step of crosslinking. This gap has a constant width which may even be maintained constant when the overall container size and volume is scaled up. This allows for constant and homogeneous process conditions independent of the scale of the used apparatus.

The insert outer wall and the body inner wall are arranged parallel with respect to each other and the distance between the body inner wall and the insert outer wall defines the width of the gap. By the term "constant width" of the gap it is understood that for every point of the surface of the insert outer wall the shortest distance to the body inner wall is constant within usual manufacturing tolerances. In particular, a tolerance is preferably less than +/−10%, more preferably less than 5% and most preferred less than 1% of the width of the gap.

Preferably, the width of the gap is in the range of from 5 mm to 100 mm, preferably from 10 mm to 80 mm and especially preferred from 20 mm to 50 mm.

Preferably, the width of the gap is chosen independently from the volume and shape of the container body so that the same width may be used for laboratory and production scale.

Preferably, the container assembly further comprises a scrapper having a cross section equivalent to the cross section of the volume defined by the insert outer wall and the body inner wall, and wherein after inserting of the container insert and before tempering the scrapper is moved along the insert outer wall and the body inner wall in order to wipe off any residual fluid.

The scrapper preferably has a shape corresponding to the shape of the gap and preferably serves as a seal to protect the fluid received in the liquid. The scrapper may, for example, be made from an elastomeric, plastic or metal material or a combination of those. In case a metal is used, the metal is preferably stainless steel.

Preferably, after scrapping, the scrapper is moved such that it rests on the fluid surface and thus covers the fluid. Advantageously, the scrapper being moved into this position protects the fluid and especially the surface of the fluid from drying.

Preferably, the container body and the container insert have a cylindrical shape and the scrapper, if present, has an annular shape. In particular, the shape of a circular cylinder is preferred, but other shapes such as rounded rectangular shapes are also possible.

In a cylindrical container shape, the cylindrical form of each of the container body and the container insert comprises an end face and in an area surrounding the edge between the lateral area and the end face the gap may have an increased width. However, for every point of the surface of the insert outer wall the shortest distance to the body inner wall is constant.

Preferably, an agitating device is provided and is inserted into the container body during the step of agitating the fluid.

The agitating device may for example comprise one, two or more kneading hooks, anchor or similar mixing blades.

Advantageously, the proposed process allows performing of the mixing and crosslinking step within the same vessel, namely the provided container body. Accordingly, the fluid comprising the precursors to be crosslinked is filled into the container body and the agitating device is provided and lowered into the container body. After mixing of the fluid by means of the agitating device, the agitating device is removed from the container body and the container insert is lowered into the container body in order to form the container assembly with the gap of constant width.

Preferably, the body inner wall and/or the insert outer wall are configured to be tempered by means of a temperature control medium.

In one embodiment, a piping system for the temperature control medium is arranged within a space defined between the body outer wall and the body inner wall of the container body and/or within a space defined by the insert outer wall of the container insert. The piping system may comprise one or more pipes and/or tubes which are preferably meander shaped.

Alternatively, the body inner wall and the body outer wall of the container body and/or the insert outer wall and a further wall of the container insert define a space for guiding the temperature control medium. Preferably, baffles are arranged within the space defined by the body outer wall and body inner wall and/or defined by the insert outer wall and the further wall. The baffles influence the flow of the temperature control medium within the defined space and avoid unwanted "shortcuts" of the temperature control medium.

In embodiments which are configured for use with a temperature control medium, the container body and the container insert preferably each comprise an inlet and an outlet for the temperature control medium.

Alternatively, electric heating elements such as thermo-electric elements or heat cartridges may be provided for tempering the insert outer wall and the body inner wall.

The container assembly preferably comprises at least one temperature sensor for monitoring the temperature of the fluid within the volume defined by the gap. The at least one temperature sensor may be provided within the container insert and/or within the container body. Also, for embodiments configured for use with a temperature control medium, temperature sensors may be provided for monitoring the inlet and/or outlet temperature of the temperature control medium.

Preferably, a control unit is provided which receives signals from the at least one temperature sensor and is configured to control the temperature of the received fluid to a predetermined temperature set point.

Preferably, the step of crosslinking is carried out at a temperature in the range of from 4° C. to 98° C., more preferably in the range of from 10° C. to 60° C. and especially preferred in the ranger of 35° C. to 55° C. Accordingly, the temperature set point is set to this crosslinking temperature at least during the step of crosslinking.

The step of crosslinking is preferably performed for a predetermined time in the range of several minutes to several days, for example from 20 minutes to 2 days. More preferably, the predetermined time is selected from the range of from 3 hours to 6 hours.

After crosslinking, the container insert is preferably removed from the container body and subsequent steps such as terminating of the crosslinking and/or dialysis or diafiltration may be performed.

In particular, it is preferred to re-insert the agitating device after crosslinking and to break up the crosslinked hydrogel.

For termination of the crosslinking the crosslinker must be removed and/or must be deactivated. It is preferred that after the step of crosslinking a substance for deactivation of the used crosslinking agent is added and mixed with the hydrogel. The used agents may then be removed by means of dialysis or diafiltration.

The termination of the crosslinking reaction is necessary since otherwise composition or hydrogels may be obtained having a viscosity or a viscosity and elasticity being too high to allow for the appropriate use, in particular as dermatological filler, respectively the viscosity or the viscoelastic properties of the composition or gel are not constant as long as the gel contains compounds that may effect crosslinking such as the crosslinker.

Basically, each compound capable of reacting with the crosslinker may be used for deactivating the crosslinker.

If a crosslinker of the epoxide type is used, termination of the crosslinking may be effected by means of the addition of compounds, which cleave the epoxide moiety such that no further crosslinking with suitable groups in the polymer can occur. Preferably, cleavage of the epoxide and thus termination of the crosslinking is effected by an acid. Organic acids as well as inorganic acids may be used for terminating of crosslinking. Preferably an inorganic acid such as hydrochloric acid is used.

Preferably, the compound used for termination of the crosslinking reaction is applied in a buffer solution. Suitable buffer solutions have been described with respect to the mixture of the polymer and water.

Alternatively, it is possible to use dialysis or diafiltration for termination of crosslinking.

In one embodiment, prior to subjecting the crosslinked hydrogel to dialysis or diafiltration, the hydrogel may be subjected to a sieving step, or several sieving steps, in order to further homogenize the product, respectively to remove inhomogeneous particles or any further particles, which might negatively affect the product, in particular when used as dermatological filler.

Preferably, dialysis comprises the steps of extruding the crosslinked hydrogel through one or more sieves, filling the sieved hydrogel into a dialysis membrane and subjecting the filled membrane to a dialysis solution, for example by placing the filled membrane into a container containing a suitable dialysis solution. A suitable dialysis solution is, for example, a solution comprising a buffer. Suitable buffers have been described with respect to the mixture of the polymer and water.

The use of sieves prior to dialysis or diafiltration may further support the efficacy of dialysis or diafiltration step. If more than one sieve is used, it is preferred that each subsequently used sieve has a smaller mesh size than the previous sieve. A typical mesh size for a first sieve is from 325 μm to 425 μm and a typical mesh size for a second sieve is in the range of from 175 μm to 225 μm.

The appropriate selection of the mesh size of the sieves further supports the removal of extraneous compounds and particles such as gelled particles, which negatively affect the desired homogeneity of the product.

Preferably, dialysis is performed by stirring the content of the container. In one embodiment, the dialysis solution may be exchanged once or at least twice by a fresh dialysis solution. In one embodiment, the interval of exchange ranges from 8 to 18 hours, or from 10 to 14 hours, such as 12±2 hours. In one embodiment, dialysis is allowed to proceed for 30 to 45 hours, or from 35 to 39 hours, such as 37±2 hours.

After dialysis or diafiltration, further steps of sieving and degassing may be performed. Also, it is possible to admix additives and to adjust the concentration of the hydrogel in the obtained composition.

Preferably, the crosslinked hydrogel is blended with a further polymer and/or at least one further component. The step of blending may be performed at any stage during the process, preferably after crosslinking has been terminated and before dialysis or diafiltration.

The further polymer is preferably a hyaluronic acid or a salt thereof.

Preferably, the further polymer has an intrinsic viscosity [η] of 1.4 m³/kg to at least 3.4 m³/kg but not limited. The molecular weight (Mw) can be calculated according to the following formula: $[η]=9.78×10^{-5}×Mw^{0.690}$ Preferably, the weight of the further polymer based on the weight of the polymer first used in the mixture is less than 5%, or less than 4%, e.g. is in the range of from 0.01 to 5%, or is in the range of from 0.1 to 4%, or is in the range of from 0.1 to 2.5%, or from 0.2 to 2.0%, or from 0.5 to 1.5%.

The at least one further component may, for example be selected from a drug. Also, for example, glycerin, buffer or salts may be selected as a further component.

Preferably, after dialysis or diafiltration, the composition obtained by the proposed process, namely the crosslinked hydrogel or a blend comprising the crosslinked hydrogel, is filled into a syringe and the syringe is sterilized. During or before filling of the blend or the crosslinked hydrogel, a local anesthetic and/or anti-arrhythmic drug may be added if necessary or desired. Such a drug may relieve itching, burning and pain, which might arise from skin inflammation when the composition according to the invention is injected into skin tissue.

Suitable drugs are known in the art.

In one embodiment, lidocaine is used as a local anesthetic and/or antiarrhythmic drug. This drug is known for e.g. injection as a dental anesthetic or as a local anesthetic for minor surgery.

In one embodiment, lidocaine is used in the form of a salt such as the hydrochloride and/or in the form of a hydrate such as the monohydrate.

Accordingly, the term "lidocaine" as used herein, encompasses the salts and hydrates thereof.

In one embodiment, lidocaine is used in an amount of from 0 to 1% by weight based on the weight of the composition or gel, or from 0 to 0.5 wt.-%. In one embodiment, the weight is from 0.3% to 0.35%. In one embodiment, the weight is 0.3% or is 0.35%.

In another embodiment, tetracaine is used. The term "tetracaine" as used herein, encompasses the salts and hydrates thereof. Tetracaine may be used in the same quantities as lidocaine.

In another embodiment, a mixture of lidocaine and tetracaine is used.

In one embodiment, the product obtained after dialysis or diafiltration is extruded into the syringe, whereby the filling of the syringe is effected. After filling, the syringe is sterilized.

The term "sterilization" as used herein encompasses any process that eliminates or removes or kills all forms of microbial life, including transmissible agents (such as fungi, bacteria, viruses, spore forms, etc.) present on the surface of the syringe and/or in the composition or hydrogel prepared according to the process of the invention. Sterilization may, for example be achieved by the methods known in the art such as applying heat or irradiation.

For example, for the production of a syringe filled with a hydrogel comprising crosslinked hyaluronic acid, the proposed process may comprise the steps of i) providing the proposed container body, ii) filing of the container body with a fluid comprising a mixture comprising non-crosslinked hyaluronic acid, a buffer and a crosslinker, iii) inserting the agitating device iv) agitating the fluid so that the mixture is homogeneous, v) removing of the agitating device, vi) providing the proposed container insert to form the container assembly, wherein the fluid is received within the gap of constant width, vii) crosslinking of the hyaluronic acid, wherein the temperature during crosslinking is controlled by tempering the insert outer wall and the body inner wall, viii) removing of the container insert, ix) re-inserting the agitating device, x) terminating crosslinking by the addition of hydrochloric acid while breaking up the hydrogel, xi) extruding of the hydrogel through at least one sieve, xii) placing the hydrogel onto a dialysis membrane, xiii) placing the filled dialysis membrane in a container filled with dialysis solution, xiv) adjustment of the hydrogel concentration in the composition, xv) sieving of the composition, xvi) degassing of the composition, xvii) extruding of the composition into syringes and xviii) sterilization of the syringes.

A further aspect of the invention may be seen in providing a composition consisting of or comprising a crosslinked hydrogel obtained by any one of the processes described herein.

Preferably, the hydrogel is based on crosslinked hyaluronic acid.

Preferably, the overall content of hyaluronic acid in the composition is in the range of from 1 to 5% by weight based on the total weight of the composition. In another embodiment, the overall content is in the range of from 1.5 to 4% by weight, or from 2 to 2.5% by weight.

A further aspect of the invention may be seen in the use of the hydrogel or a composition comprising the hydrogel obtained by the described method in a cosmetic application or as a dermatological filler.

EXAMPLES

Compositions comprising hyaluronic acid have been prepared according to the described process. In a first example, a container body having a volume of 20 l was used. In a second example, a container body having a volume of 3 l was used. The stated volume of the container body refers to the volume with removed container insert.

The synthesis was performed using the inventive container assembly according to the following steps:

In a first step, a phosphate buffer solution having a pH of 7.1 and a hyaluronic acid (355.36 g and 118.45 g for 20 l and 3 l respectively) having a density of 2.80 m³/kg were mixed in the container body and pre-swelling and homogenization of the hyaluronic acid was performed. Subsequently, NaOH (28.69 and 9.56 g for 20 l and 3 l respectively) and BDDE (42.66 g and 14.22 g for 20 l and 3 l respectively) (1,4-butanediol diglycidylether) were added and homogenization was continued. After homogenization, crosslinking of the mixture was performed at a temperature of 40° C. for 3.5 hours, with the container insert and the container body forming a volume having a constant width. Subsequently, the container insert was removed and crosslinking was stopped by neutralization by addition of HCl (673.2 g and 224.4 g for 20 l and 3 l respectively) and a buffer (1059.54 g and 353.18 g for 20 l and 3 l respectively) to adjust the pH to about 7. The mixture was homogenized and subsequently subjected to dialysis for 3.41 and 4.20 for 20 l and 3 l respectively hours (this time correlates to 7 DCF chamber volumes), wherein a phosphate buffer solution was added. After dialysis, screening and homogenization was performed and the mixture was blended with lidocaine hydrochloride. After a further step of screening, the blended mixture was filled into syringes and the filled syringes were sterilized.

In both examples, a hydrogel free of particles was obtained. The rheological properties of the hydrogels are listed in table 1.

TABLE 1

| | Container volume [l] | HA concentration [mg/g] [Lot. PHI3678] | Storage modulus (G') [Pa] | Loss factor (tanδ) [—] | Complex viscosity (η*) [Pa*s] |
|---|---|---|---|---|---|
| Example 1 | 20 | 23.54 ± 0.25 | 346 ± 2 | 0.19 ± 0.00 | 56.0 ± 0.3 |
| Example 2 | 3 | 23.54 ± 0.08 | 339 ± 5 | 0.19 ± 0.01 | 54.8 ± 0.8 |

The rheological measurements were performed using a parallel plate rheometer. The PP (plate-plate) distance was set to 35 mm. Measurements were performed at a temperature of 25° C. A frequency sweep test was performed in the frequency range from 0.1 Hz to 10 Hz and having constant deformation (y) of 0.1%. Evaluation was carried out at 1.0 Hz. This method is valid only for the products whose LVE (linear viscoelastic) area is <5% at these conditions.

BRIEF DESCRIPTION OF THE FIGURES

The Drawings Show

FIG. 1 shows a cross-sectional view of a container body 2 for use in the described process for producing crosslinked hydrogels. The container body 2 as shown in FIG. 1 has a circular cylindrical shape and has a body inner wall 21 and a body outer wall 22. Within a space defined by the body inner wall 21 and the body outer wall 22, means for tempering of the body inner wall 21 are arranged which are not shown in the schematic view of FIG. 1. The means for tempering are, for example, a piping system for a temperature control fluid which is in contact with the body inner wall 21. A fluid 7 is received in the container body 2.

The fluid 7 is, for example, a precursor for the production of a hydrogel and may, for example, comprise a mixture of hyaluronic acid, water and a crosslinker.

Figure 1:
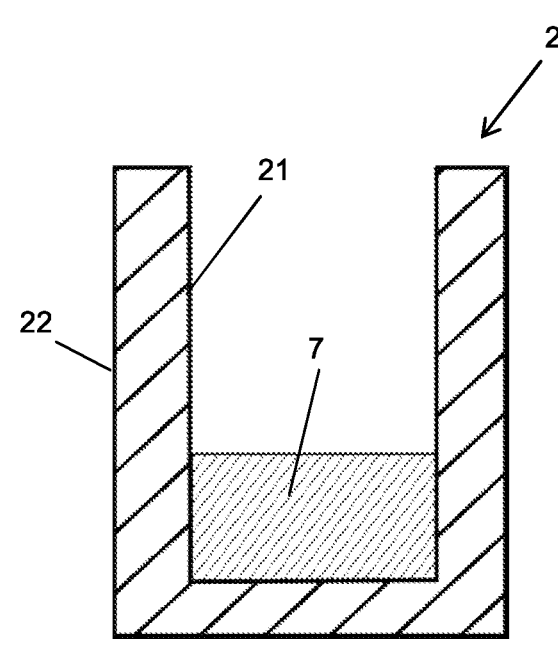
FIG. 1 a cross-sectional view of a container body.
Figure 2:
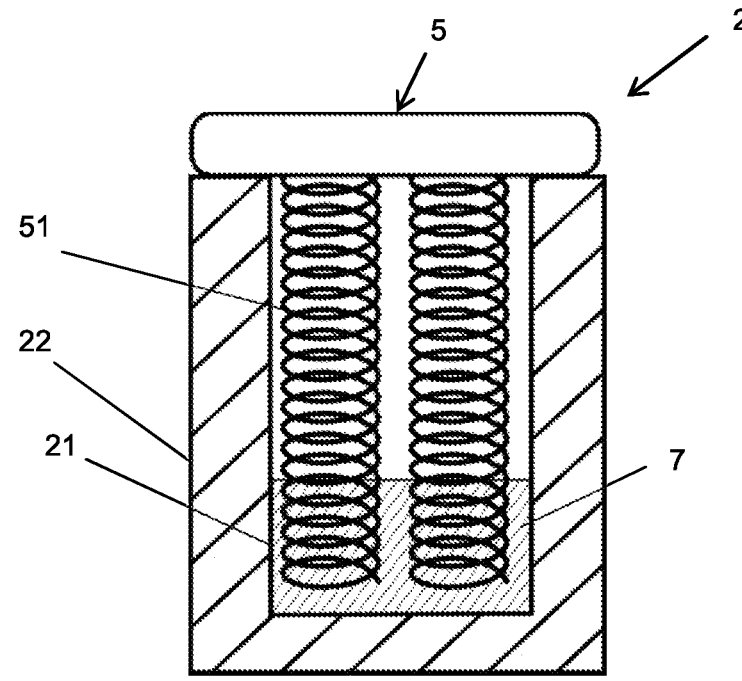
FIG. 2 a cross-sectional view of the container body and an agitator.

FIG. 2 shows a cross-sectional view of a container body 2 as described with respect to FIG. 1, wherein an agitator 5 has been inserted into the container body. The agitator 5 comprises in the shown example embodiment two kneading hooks 51 which engage the container body 2 and are partially submerged in the fluid 7 received in the container body 2.

By means of the agitator 5 the fluid 7 may be homogenized.

Figure 3:
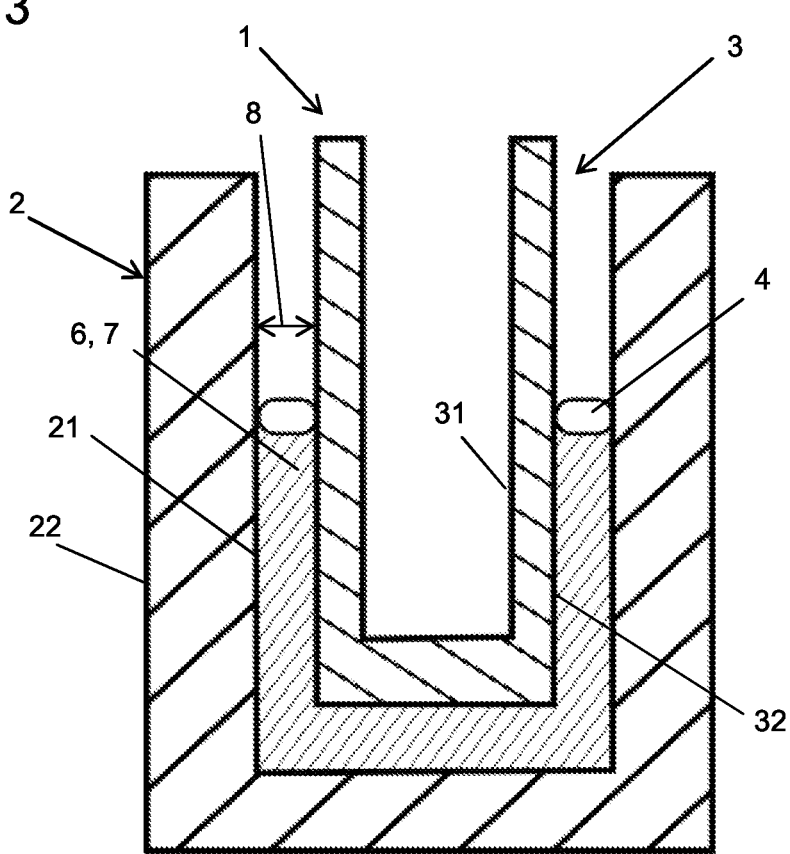
FIG. 3 a cross-sectional view of a container assembly comprising the container body and a container insert, FIG. 4 a diagram showing the temperature inside different container assemblies, and FIG. 5 product comprising over-crosslinked particles when prepared according to the prior art.

FIG. 3 shows a container assembly 1 comprising the container body 2 as described with respect to FIG. 1 and a container insert 3. The container insert 3 comprises an insert outer wall 32 and an insert further wall 31. Within a space defined by the insert further wall 31 and the insert outer wall 32, means for tempering of the insert outer wall 32 are arranged which are not shown in the schematic view of FIG. 1. The means for tempering are, for example, a piping system for a temperature control fluid which is in contact with the insert outer wall 32.

In the situation shown in FIG. 3, the container insert 3 has been inserted into the partially filled container body 2 so that the fluid 7 is partially displaced by the container insert 3. The insert outer wall 32 and the body inner wall 21 are arranged parallel with respect to each other and the distance between the body inner wall 21 and the insert outer wall 32 defines the width of a gap 8. The gap 8 defines a volume 6 which receives the fluid 7.

The container assembly 1 further comprises a scrapper 4. The scrapper 4 has a cross section equivalent to the cross section of the volume defined by the insert outer wall 32 and the body inner wall 21. The scrapper 4 may be moved along the insert outer wall 32 and the body inner wall 21 in order to wipe off any residual fluid 7.

In the situation shown in FIG. 3, the scrapper 4 has been moved such that it rests on the fluid surface and thus covers the fluid 7.

The space defined by the gap 8 is formed such that every part of the volume of the fluid 7 is located near one of the tempered surfaces, namely the body inner wall 21 and the insert outer wall 32. Thus, the entire volume of the liquid 7 will easily arrive at a set temperature with minimal temperature gradient so that the temperature of the liquid 7 is nearly homogeneous.

Figure 4:
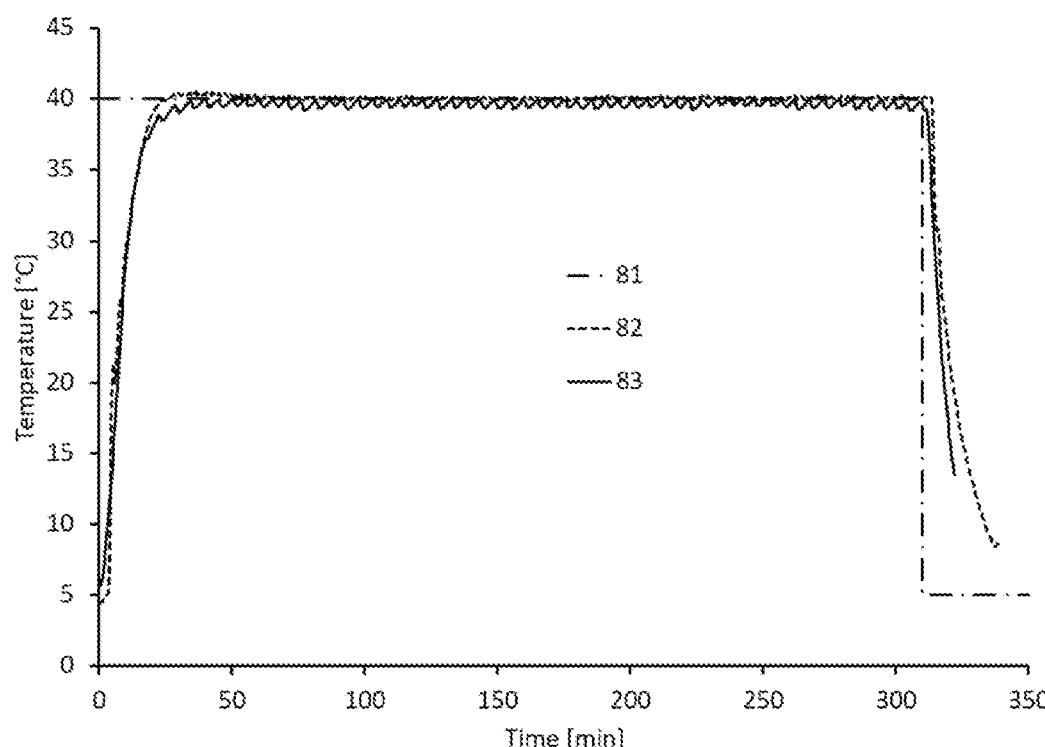

The diagram of FIG. 4 shows the temperature vs. time for two different container assemblies 1. The sensor used for temperature measurement was located within the volume formed by the gap. For temperature control, a different sensor is used which is preferably arranged at or near the inner wall 22 of the container body 2. A first curve 82 shows the temperature of a first container assembly 1 having a volume of 20 l. A second curve 83 shows the temperature of a second container assembly 1 having a volume of 3 l. The volume refers in each case to the volume of the container body 2 with the container insert 3 removed. A third curve 81 shows the temperature set point which in this example was first set to 40° C. and then reduced to 5° C. after completion of the crosslinking.

Figure 5:
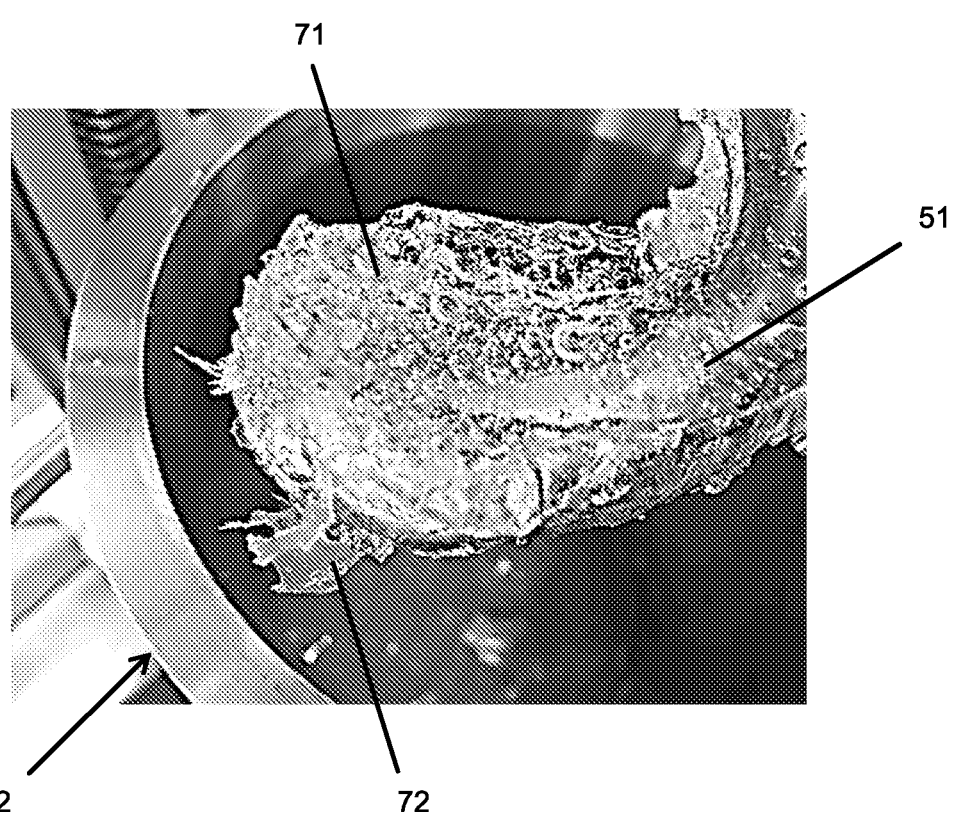

FIG. 5 shows a picture of the production of a hydrogel with a process not according to the invention. In particular a conventional mixing vessel having only a container body 2 is used. No container insert 3 is provided. Without the use of the container insert 3, tempering of the fluid may only be effected by tempering the inner wall of the mixing vessel. Accordingly, there is a large temperature gradient within the received fluid.

Due to the temperature gradient, the crosslinking reaction is non-homogeneous. Due to evaporation (i.e. dehydration) on the gel surface the crosslinking reaction becomes more intense and solid particles form. In the picture of FIG. 5, a kneading hook 51 is just removed from the mixing vessel. Crosslinked hydrogel 71 having particles 72 are visible. These particles do not dissolve in the subsequent process and lead to rejects in the final product. The production of such particles 72 may be avoided by means of the proposed process making use of the container insert 3 during the step of crosslinking.

LIST OF REFERENCE NUMERALS

1 container assembly
    2 container body
    3 container insert
    4 scrapper
    5 agitator
    6 volume for receiving fluid
    7 fluid
    8 gap
    21 container body inner wall
    22 container body outer wall
    23 container body temperature control medium inlet
    24 container body temperature control medium outlet
    31 container insert further wall
    32 container insert outer wall
    51 kneading hooks
    71 crosslinked product
    72 over-crosslinked particles
    81 temperature set point
    82 temperature 201 container
    83 temperature 31 container

The invention claimed is:

1. A process for producing a composition comprising a crosslinked hydrogel, the process comprising the steps of
    providing a container body, wherein the container body has a body inner wall and a body outer wall, wherein the body inner wall is configured to be tempered by means of temperature control arranged within a space defined between the body outer wall and the body inner wall of the container body,
    filling with a fluid comprising at least a mixture of a polymer and water into the container body,
    agitating the fluid,
    providing a container insert, the container insert having an insert outer wall which is configured to be tempered by means of temperature control arranged within a space defined within the insert outer wall of the container insert,
    forming a container assembly by inserting the container insert into the container body so that the insert outer wall of the container insert and the body inner wall of the container body are separated by a gap of constant width that defines a volume for receiving the fluid, and
    crosslinking the fluid while tempering the insert outer wall by the means of the temperature control arranged within the space defined within the insert outer wall of the container insert and, while tempering the body inner wall by the means of temperature control arranged within the space defined between the body outer wall and the body inner wall of the container body to form a crosslinked hydrogel, wherein the fluid is not agitated during the crosslinking to obtain the crosslinked hydrogel free of solid particles formed during the step of crosslinking.

2. The process of claim 1, wherein the container assembly further comprises a scrapper having a cross section equivalent to the cross section of the volume defined by the insert outer wall and the body inner wall, and wherein after inserting of the container insert and before tempering the scrapper is moved along the insert outer wall and the body inner wall in order to wipe off any residual fluid.

3. The process of claim 2, wherein, after scrapping, the scrapper is moved such that it rests on the fluid surface and thus covers the fluid.

4. The process of claim 1, wherein the container body and the container insert have a cylindrical shape and the scrapper, if present, has an annular shape.

5. The process of claim 1, wherein an agitating device is provided and is inserted into the container body during the step of agitating the fluid, wherein the agitating device is removed from the container body before the container insert is inserted into the container body.

6. The process of claim 5, wherein the agitating device comprises at least one kneading hook, anchor, or mixing blade.

7. The process of claim 1, wherein the insert outer wall, and the body inner wall, are configured to be tempered by a temperature control medium.

8. The process of claim 7, wherein a piping system for the temperature control medium is arranged within the space defined within the insert outer wall of the container insert, and within the space defined between the body outer wall and the body inner wall of the container body.

9. The process of claim 7, wherein the insert outer wall and a further wall of the container insert define a space for guiding the temperature control medium, and wherein the body inner wall and the body outer wall of the container body define a space for guiding the temperature control medium.

10. The process of claim 9, wherein baffles are arranged within the space defined by the insert outer wall and the further wall, and wherein baffles are arranged within the space defined by the body outer wall and the body inner wall.

11. The process of claim 1, wherein the width of the gap is in the range of from 5 mm to 100 mm.

12. The process of claim 1, wherein the step of crosslinking is carried out at a temperature in the range of 4° C. to 98° C.

13. The process of claim 1, wherein the polymer is a hyaluronic acid and/or a sodium salt thereof.

14. The process of claim 1, wherein after crosslinking the container insert is removed from the container body.

15. The process of claim 1, wherein, after crosslinking, the crosslinking is terminated and the crosslinked hydrogel is subsequently subjected to dialysis or diafiltration or the crosslinked hydrogel is subjected to dialysis or diafiltration for termination of crosslinking.

16. The process of claim 15, wherein the crosslinked hydrogel is blended with a further polymer and/or at least one further component.

17. The process of claim 15, wherein, after dialysis or diafiltration, the crosslinked hydrogel or a blend comprising the crosslinked hydrogel is filled into a syringe and the syringe is sterilized.

18. The process of claim 16, wherein, after dialysis or diafiltration, the crosslinked hydrogel or a blend comprising the crosslinked hydrogel is filled into a syringe and the syringe is sterilized.

19. A composition comprising a crosslinked hydrogel obtained by a process of claim 1.

20. A method for treating a subject in need thereof, comprising applying the composition of claim 19 in a cosmetic application or as a dermatological filler to the subject.

\* \* \* \* \*